United States Patent [19]
Burgos et al.

[11] Patent Number: 5,366,693
[45] Date of Patent: Nov. 22, 1994

[54] AIR/STEAM/LIQUID EXHAUST DEVICE FOR SINGLE CYCLE PRESSURE VESSEL

[75] Inventors: Mel-Angeli M. Burgos, Bellflower, Calif.; Charles H. Feathers, III, Hilton, N.Y.; John C. Schmoegner, Redondo Beach, Calif.

[73] Assignee: MDT Corporation, Torrance, Calif.

[21] Appl. No.: 822,939

[22] Filed: Jan. 21, 1992

[51] Int. Cl.5 .................................................. A61L 2/00
[52] U.S. Cl. ...................................... 422/26; 422/110; 422/114; 422/298
[58] Field of Search ..................... 422/26, 38, 39, 295, 422/298, 299, 305, 307, 108, 110, 112, 114; 48/173; 55/18, 160, 210

[56] References Cited

U.S. PATENT DOCUMENTS

| | | | |
|---|---|---|---|
| 4,164,538 | 8/1979 | Young et al. | 422/26 |
| 4,325,906 | 4/1982 | Kackos | 422/26 |
| 4,865,814 | 10/1989 | Childress | 422/116 |
| 4,891,188 | 1/1990 | Albright et al. | 422/114 |
| 4,971,764 | 11/1990 | Albright | 422/110 |
| 5,132,084 | 7/1992 | Harrell et al. | 422/26 |
| 5,149,507 | 9/1992 | Ellis, Jr. | 422/112 |

*Primary Examiner*—Robert J. Warden
*Assistant Examiner*—Robert Carpenter
*Attorney, Agent, or Firm*—Trask, Britt & Rossa

[57] ABSTRACT

A pressure vessel in which the air steam and liquid exhaust systems are combined and wherein all exhaust systems are directed through a water reservoir, using a single control valve and a temperature/pressure sensor in the system.

16 Claims, 1 Drawing Sheet

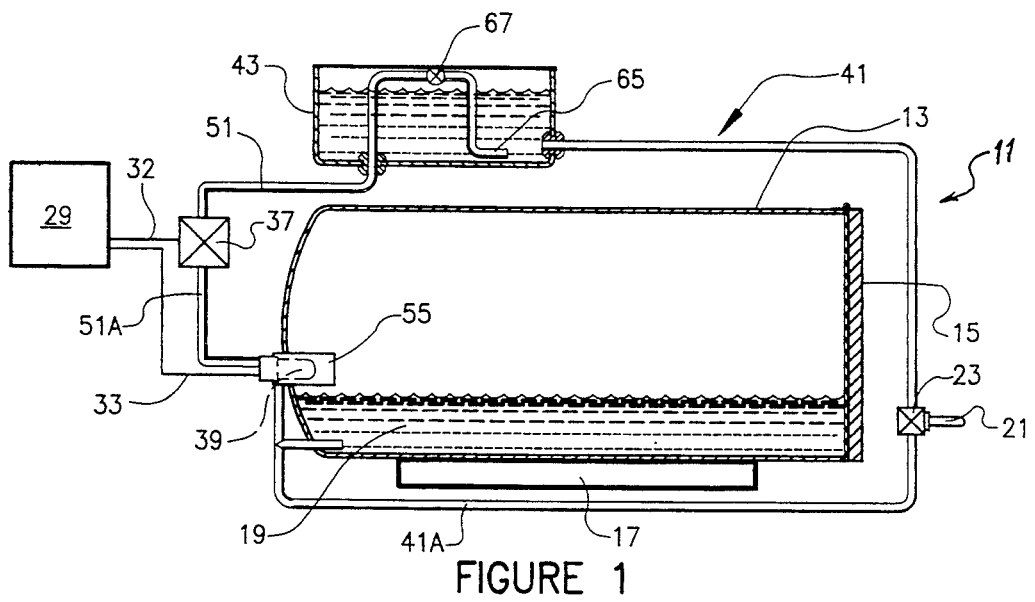
FIGURE 1
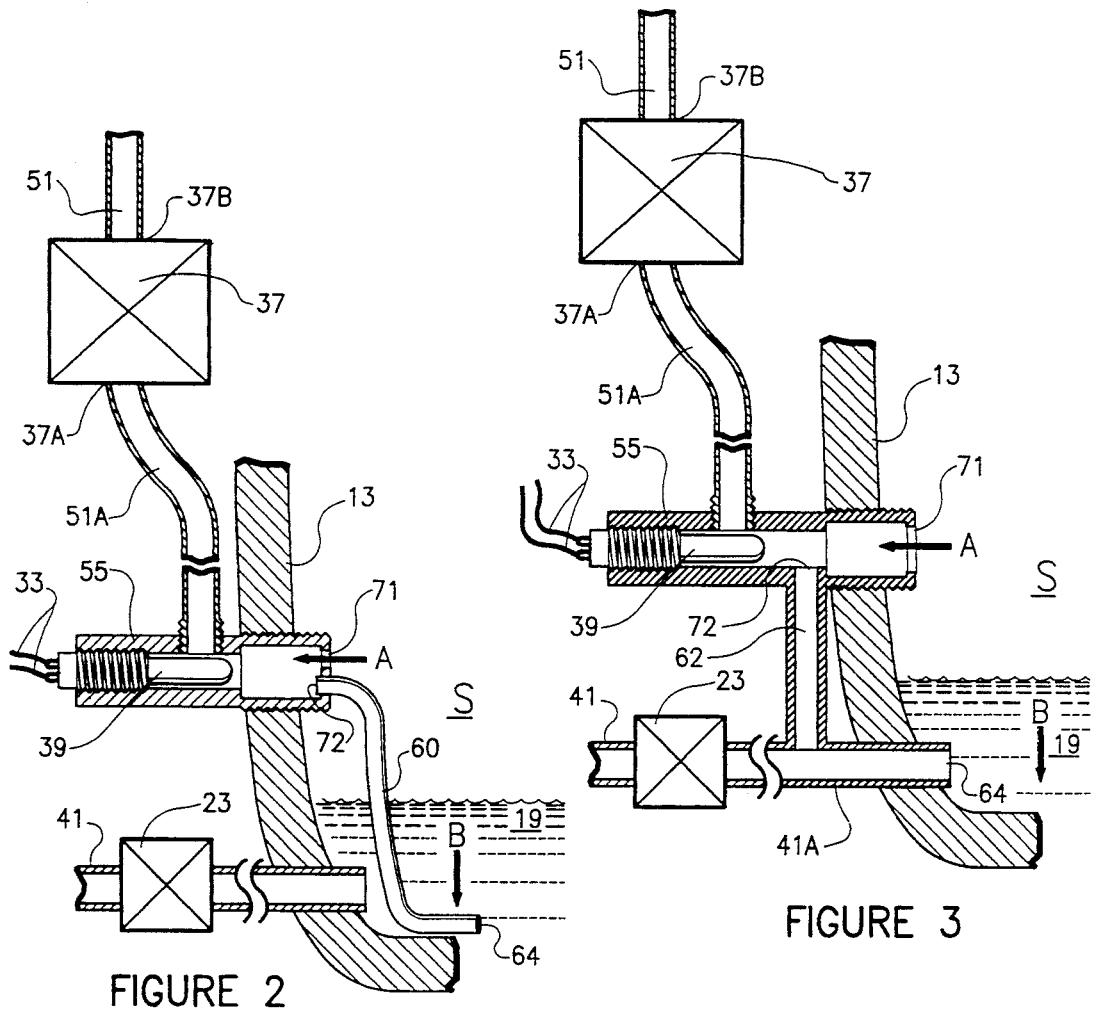
FIGURE 2
FIGURE 3

AIR/STEAM/LIQUID EXHAUST DEVICE FOR SINGLE CYCLE PRESSURE VESSEL

BACKGROUND

1. Field

This invention relates to the exhaust systems of pressure vessels, notably single cycle steam sterilizers. It provides a simplified system for the exhaust of air, steam and liquid from such vessels.

2. State of the Art

Pressure vessels, such as those applied to steam sterilization, are often operated in a fashion which requires sequential exhaustion of air and steam and/or liquid (such as water or chemical solutions). Representative of such vessels are those included in fixed cycle steam sterilizers. A typical cycle for such a sterilizer embodied as a self-contained, table top device involves exhausting air from the pressure vessel at the beginning of the cycle through a first conduit and valve system. Steam and liquid are then exhausted through a second conduit and valve system at the end of the cycle. The valves may be controlled by solenoids responsive to temperature and/or pressure probes. The valve in the air exhaust system ordinarily requires a steam trap or its equivalent because the exhausted air inevitably contains some steam.

There are currently available a number of fixed cycle table top sterilizers designed for use in medical and dental offices, hospitals, clinics, laboratories and other facilities where a variety of materials require sterilization processing. Such sterilizers can be used for processing either wrapped or unwrapped instruments, test tubes, and petri dishes, among other things. This equipment is subject to stringent manufacturing standards. It is used in environments which demand safe and reliable operation. There is a continuing strong interest in modifying these devices in ways which will simplify their operation and/or reduce their cost without compromising the safety or reliability of their operation.

A sterilizer cycle typically starts with placing a load into the sterilizer chamber, adding the proper amount of water to the chamber, closing and latching the chamber door and pushing a start button. The chamber is then heated, usually by means of induction coils. As steam is generated within the chamber, it displaces air through an exhaust conduit communicating with the chamber above water level. The air exhaust conduit typically communicates through a solenoid valve or steam trap which closes once the air is exhausted from the chamber. Eventually, the prescribed exposure temperature is achieved within the chamber, and timing of the exposure stage of the cycle begins. At the close of the exposure stage, the steam exhaust valve is opened, and steam and excess water are exhausted through a second conduit system communicating with the bottom of the chamber.

The valving, controls, conduits and associated components of air, steam and excess water exhaust systems represent a significant portion of the manufacturing costs of table top sterilizers. The simplification of these systems would constitute a significant improvement.

SUMMARY OF THE INVENTION

According to this invention, the air, steam and liquid exhaust systems of a table top sterilizer are combined to eliminate a number of component parts previously regarded as essential to such equipment. Ideally, all exhaust streams are directed through a water reservoir. Such a reservoir is normally associated with the sterilizer in any event, and its use in accordance with this invention avoids the necessity for a separate steam trap. Combining the exhaust conduits also avoids the need for duplicating solenoid control valves and the associated fixtures. According to this invention, all exhaust venting is done through a single valve and conduit system.

This invention is particularly applicable to process systems of the type in which liquid is introduced to a pressure vessel to a selected liquid level at the beginning of a cycle. The vessel is then operated to create vapors in its interior, whereby to first displace air from the vessel, to then elevate the pressure within the vessel and to thereafter displace vapors and/or liquid from the vessel. The improved exhaust system of this invention generally comprises a valve, including an inlet, an outlet and control means and drive means for selectively operating the valve between respective open and closed conditions. A first passageway connects the outlet to a target region, such as a liquid reservoir. A second passageway connects the inlet to the interior of the vessel above the liquid level. A third passageway connects the inlet to the interior of the vessel near the bottom of its interior. The valve is open during the phases of the cycle in which air or vapor/liquid is being displaced. It is closed while pressure is being elevated and during the actual processing phases of the cycle which are conducted at elevated pressure.

While other liquids, such as chemical sterilants or reactants, are within contemplation, the liquid introduced to the vessel is ordinarily water, usually distilled or deionized water. The term "vapor" is used in this disclosure to include steam, gasses and any combination of these or other substances having fluidity properties similar to those of steam.

The invention may be embodied in various arrangements. While it may find application in other types of pressure vessels, it is of current interest in connection with sterilization chambers which are operated at positive pressure throughout a complete cycle. Positive pressure is relied upon both to exhaust air at the commencement of the cycle and to exhaust vapor and liquid at the end of the cycle. The exhaust system of this invention may be incorporated in sterilization vessels which are programmable to run cycles selected from a menu, but is most advantageously used with fixed cycle sterilizers. The exhaust system may then include a single control valve which is held open or closed in response to sensed pressure and temperature conditions within the chamber, being finally opened after a selected timed exposure period.

BRIEF DESCRIPTION OF THE DRAWINGS

In the drawings, which illustrate what is presently regarded as the best mode for carrying out the invention:

FIG. 1 is a schematic view in side elevation of a typical fixed cycle, table top sterilizer including an exhaust system of this invention;

FIG. 2 is a fragmentary view in section illustrating one embodiment of the invention; and FIG. 3 is a view similar to FIG. 2, illustrating an alternative embodiment of the invention.

DESCRIPTION OF THE ILLUSTRATED EMBODIMENTS

A table top sterilizer, designated generally 11, includes a pressure vessel 13, with a latchable door 15. A heating coil 17 is mounted adjacent the vessel 13 as shown to heat water 19 pooled above the heater 17. A manually-operated fill button 21 is mounted on the door to control a valve 23 through which an appropriate amount of liquid is supplied to the vessel. A controller 29 is connected by wires 32 and 33 to a solenoid valve 37 and a temperature/pressure probe 39, respectively. A fill conduit 41 directs water or other liquid from a reservoir 43 through the valve 23 controlled by fill button 21 (when in open condition) and the line 41A to the bottom of the interior of the vessel 13. Air, steam and/or liquid may be exhausted through the exhaust conduit 51 when the valve 37 is in its open condition.

The valve 23 is typically manually operated. In any event, a cycle is commenced by admitting an appropriate quantity of liquid to the vessel manually through the fill valve 23 after door 15 is closed and secured. The valve 23 is then closed and the heater 17 is turned on, either manually or by the controller 29. At the beginning of the cycle, the valve 37 is open. Accordingly, as the heater 17 vaporizes the water 19, steam S displaces air from the vessel 13 as indicated by the arrow A in FIGS. 2 and 3. The displaced air is exhausted through the valve 37 and the conduit 51 until the probe 39 senses temperature, time and pressure conditions indicative of the absence of air. The valve 37 is then closed by the controller, in response to signals from probe 39. Continued heating results in further pressure elevation within the vessel 13. When the probe 39 senses the pressure appropriate for the processing phase of the cycle, timing of the processing phase is begun. At the end of the processing phase, the valve 37 is again opened, e.g., by the controller 29. The positive pressure within the vessel 13 then forces steam S in the directions indicated by the arrows A and B in FIGS. 2 and 3. Any excess liquid 19 is thereby forced up the conduit 60, in the case of the embodiment illustrated by FIG. 2 or back through the fill conduit 41A and the vertical conduit 62, in the case of the embodiment illustrated by FIG. 3. In either case, steam and liquid are exhausted through a chamber 55, the valve 37 and the conduit 51.

Complete evacuation of liquid is important because the cycle usually includes a drying phase following the exposure phase. For that reason, the entry 64 to the passageway for liquid (and at least some vapor) from the interior of the vessel 13 to the inlet 37A of the valve 37 is preferably adjacent the bottom of the interior of pressure vessel 13, as shown.

The terminal end 65 of the conduit 51 extending from the outlet 37B of the valve 37 is configured as a steam trap which includes an antisiphon valve 67. A suitable such valve 67 may comprise a simple orifice closed by a floating or spring biased ball. In any event, the valve operates to close when the pressure within the conduit 51 exceeds ambient pressure and to open when the pressure within conduit 51 is below ambient.

As illustrated, a first passageway 51 connects the outlet 37B of the valve 37 to a target (reservoir 43). A second passageway for air (and vapor) provides fluid communication between the inlet 37A of the valve 37 and the interior of the vessel through the conduit segment 51A, chamber 55 and port 71. A third passageway provides fluid communication for liquid (and vapor) between the inlet 37A of the valve 37 and the interior of the vessel 13 through the conduit segment 51A, the chamber 55 and the travel path provided between the proximal 72 and terminal 64 ends of the conduit 60 (FIG. 2) or the conduits 62, 41A (FIG. 3). The chamber 55 is thus in fluid communication with the vessel 13 through separate isolated travel paths. Air is displaced at the beginning of the cycle at pressures close to ambient, but in any event insufficient to force liquid from the vessel 13 into the chamber 55. At the end of the processing phase of the cycle, the pressure in the vessel is sufficient that when the valve 37 is placed in open condition, any liquid pooled on the bottom of the vessel is forced out through the third passageway, chamber 55 and the valve 37.

Reference in this disclosure to details of the illustrated embodiments is not intended to limit the scope of the appended claims which are intended to define the invention, including equivalents to the illustrated embodiments.

What is claimed is:

1. An improved exhaust structure for a pressure vessel within a system, said system being structured and arranged such that liquid is introduced to said vessel to a selected liquid level and vapors are created within said vessel to first displace air from said vessel, to then elevate the pressure within said vessel and to thereafter displace vapors and/or liquid from said vessel, said improved exhaust structure comprising:
   a valve, including an inlet, an outlet and drive means for selectively operating said valve between respective open and closed conditions;
   a first passageway connecting said outlet to a receiver;
   a second passageway fluidly connecting said inlet to the interior of said vessel above said liquid level; and
   a third passageway fluidly connecting said inlet to the interior of said vessel at the bottom of said interior.

2. An improved exhaust structure according to claim 1 wherein said second and third passageways include a common chamber connected in fluid communication through said second passageway to said inlet, said chamber also being in fluid communication with the interior of said vessel, said chamber also providing an opening for said second passageway to the interior of said vessel above said liquid level.

3. An improved exhaust structure for a pressure vessel within a system, said system being structured and arranged such that liquid is introduced to said vessel to a selected liquid level and vapors are created within said vessel to first displace air from said vessel, to then elevate the pressure within said vessel and to thereafter displace vapors and/or liquid from said vessel, said improved exhaust structure comprising:
   a valve, including an inlet., an outlet and drive means for selectively operating said valve between respective open and closed conditions;
   a first passageway fluidly connecting said outlet to a receiver;
   a second passageway fluidly connecting said inlet to the interior of said vessel above said liquid level; and
   a third passageway connecting said inlet to the interior of said vessel at the bottom of said interior;
   wherein said second and third passageways include a common chamber connected in fluid communication through said second passageway to said inlet, said common chamber also being in fluid communication with the interior of said vessel and providing an opening for said second passageway to the interior of said vessel above said liquid level, said common chamber further including a sensor probe mounted in said common chamber to detect temperature and/or pressure conditions within said vessel, an electronic controller connected to receive signals from said probe and means associated with said controller for operating said drive means in order to open and close said valve in response to said signals.

4. An improved exhaust structure according to claim 1 wherein said first passageway from said outlet terminates in an open end immersed in a pool of liquid in a means of containment in said receiver.

5. An improved exhaust structure for a pressure vessel within a systems, said system being structured and arranged such that liquid is introduced to said vessel to a selected liquid level and vapors are created within said vessel to first displace air from said vessel, to then elevate the pressure within said vessel and to thereafter displace vapors and/or liquid from said vessel, said improved exhaust structure comprising:

a valve, including an inlet, an outlet and drive means for selectively operating said valve between respective open and closed conditions;

a first passageway fluidly connecting said outlet to a receiver;

a second passageway fluidly connecting said inlet to the interior of said vessel above said liquid level; and a third passageway connecting said inlet to the interior of said vessel at the bottom of said interior;

wherein said first passageway from said outlet terminates in an open end immersed in a pool of liquid in a means of containment in said target region, and said means of containment is a reservoir in fluid communication with said vessel through a conduit which provides means to introduce liquid to said vessel.

6. An improved exhaust structure according to claim 5 wherein said second and third passageways further include a common chamber fluidly connected through said second passageway to said inlet, said chamber also being in fluid communication with the interior of said vessel, said chamber also providing an opening for said second passageway to the interior of said vessel above said liquid level.

7. An improved exhaust structure according to claim 6 including a sensor probe mounted in said common chamber to detect temperature and/or pressure conditions within said vessel, an electronic controller connected to receive signals from said probe and means associated with said controller for operating said drive means to open and close said valve in response to said signals.

8. In a system including a pressure vessel, means to introduce liquid into said pressure vessel to a selected liquid level and means to operate said vessel to first displace air from the vessel and to thereafter displace vapors and/or liquid from the vessel; an improved exhaust structure from said vessel comprising:

a valve having an inlet and an outlet and drive means for opening and closing said valve;

a receiver for exhaust fluids passed through the valve;

first means for connecting the outlet of said valve with said receiver;

second means for fluidly connecting the inlet of said valve to the interior of said pressure vessel above the selected liquid level; and third means for fluidly connecting the inlet of said valve to the interior of said pressure vessel at the bottom thereof.

9. The improved exhaust structure of claim 8, wherein said second means and said third means further include a common chamber and a passageway interconnecting said chamber and the inlet of said valve.

10. The improved exhaust structure of claim 9, wherein said second means further includes a passageway interconnecting said chamber and the interior of said pressure vessel; and said third means further includes a separate passageway interconnecting said chamber and the interior of said pressure vessel.

11. In a system including a pressure vessel, means to introduce liquid into said pressure vessel to a selected liquid level and means to operate said vessel to first displace air from the vessel and to thereafter displace vapors and/or liquid from the vessel; an improved exhaust structure from said vessel comprising:

a valve having an inlet and an outlet and drive means for opening and closing said valve;

a receiver for exhaust fluids passed through the valve;

first means for connecting the outlet of said valve with said receiver;

second means for fluidly connecting the inlet of said valve to the interior of said pressure vessel above the selected liquid level; and third means for fluidly connecting the inlet of said valve to the interior of said pressure vessel at the bottom thereof;

wherein said second means and said third means further include a common chamber and a passageway interconnecting said chamber and the inlet of said valve, and said second means further includes a passageway interconnecting said chamber and the interior of said pressure vessel; and said third means further includes a separate passageway interconnecting said chamber and the interior of said pressure vessel; and further including:

a pressure and temperature sensing probe extending into said chamber to sense pressure and/or temperature therein; and means for connecting the pressure and temperature sensing probe through an electronic controller to the drive means of said valve, whereby said valve is opened and closed by said drive means in accordance with pressure and/or temperature sensed by said probe.

12. The improved exhaust structure of claim 11, wherein said receiver for fluids passed through the valve further comprises:

a reservoir at least partially filled with liquid;

wherein said first means for connecting the outlet of said valve with said receiver further includes a conduit having one end connected to the outlet of the valve and another end terminating near the bottom of said reservoir, and an antisiphon valve is positioned in said conduit above the level of liquid in said reservoir.

13. The improved exhaust structure of claim 12, wherein liquid introduced to the pressure vessel is supplied through a passageway from the same said reservoir as is used as a receiver for exhaust fluids.

14. The improved exhaust structure of claim 13, further including a conduit supplying liquid to the pressure vessel from the reservoir and a manually-operated valve in the conduit to control flow therethrough.

15. In a system including a pressure vessel, means to introduce liquid into said pressure vessel to a selected liquid level and means to operate said vessel to first displace air from the vessel and to thereafter displace vapors and/or liquid from the vessel; an improved exhaust structure from said vessel comprising:

a valve having an inlet and an outlet and drive means for opening and closing said valve;

a receiver for exhaust fluids passed through the valve;

first means for connecting the outlet of said valve with said receiver;

second means for fluidly connecting the inlet of said valve to the interior of said pressure vessel above the selected liquid level; and third means for fluidly connecting the inlet of said valve to the interior of said pressure vessel at the bottom thereof;

wherein said second means and said third means further include a common chamber and a passageway interconnecting said chamber and the inlet of said valve, said common chamber further including:

a pressure and temperature sensing probe extending into the chamber to sense pressure and/or temperature therein; and said probe including:

means for connecting said pressure and temperature sensing probe to the drive means of the valve, whereby the valve is opened and closed by said drive means in accordance with pressure and/or temperature sensed by said probe.

16. In a system including a pressure vessel, means to introduce liquid into said pressure vessel to a selected liquid level and means to operate said vessel to first displace air from the vessel and to thereafter displace vapors and/or liquid from the vessel; an improved exhaust structure from said vessel comprising:

a valve having an inlet and an outlet and drive means for opening and closing said valve;

a receiver for exhaust fluids passed through the valve;

first means for connecting the outlet of said valve with said receiver;

second means for fluidly connecting the inlet of said valve to the interior of said pressure vessel above the selected liquid level; and third means for fluidly connecting the inlet of said valve to the interior of said pressure vessel at the bottom thereof;

wherein the receiver for fluids passed through the valve further comprises:

a reservoir at least partially filled with liquid;

wherein the means for connecting the outlet of said valve with the receiver further includes a conduit having one end connected to the outlet of the valve and another end terminating at a bottom of said reservoir; and a stream trap in the conduit and having an antisiphon valve therein positioned at least partially above the level of liquid in the reservoir.

* * * * *